US005882657A

United States Patent [19]
Miguel-Colombel et al.

[11] Patent Number: 5,882,657
[45] Date of Patent: Mar. 16, 1999

[54] COSMETIC COMPOSITION IN THE FORM OF A SOFT PASTE, A PROCESS FOR ITS PREPARATION AND ITS USE

[75] Inventors: Dolorès Miguel-Colombel, L'Hay-les-Roses; Véronique Jacques, Bourg la Reine, both of France

[73] Assignee: L'Oreal, Paris, France

[21] Appl. No.: 655,920

[22] Filed: May 31, 1996

[30] Foreign Application Priority Data

Jun. 2, 1995 [FR] France .................................. 95 06606

[51] Int. Cl.$^6$ ............................. A61K 6/00; A61K 7/00; A61K 7/025
[52] U.S. Cl. ............................... 424/401; 424/61
[58] Field of Search ................. 424/401, 59, 64; 514/844, 845, 947

[56] References Cited

U.S. PATENT DOCUMENTS 4,431,673   2/1984   Goldner et al. .................. 424/365
5,225,186   7/1993   Castrogiovanni et al. .

FOREIGN PATENT DOCUMENTS

A-0462709   12/1991   European Pat. Off. .
0 522624A1   6/1992   European Pat. Off. .
A-2486800    1/1982   France .
612 36716   10/1986   Japan .

OTHER PUBLICATIONS

English language Derwent Abstract of FR-A-2486800.
Manufacturing Chemist, "Lip Products," 58(8) : 65 (1987).

*Primary Examiner*—Thurman K. Page
*Assistant Examiner*—Sharon Howard
*Attorney, Agent, or Firm*—Finnegan, Henderson, Farabow, Garrett & Dunner, L.L.P.

[57] ABSTRACT

A cosmetic composition in the form of a soft paste, comprising at least one wax and at least one oil, wherein the at least one oil is thickened by the presence of at least one thickener and at least 6% by weight of at least one filler. A process for the preparation of this composition, as well as its use in cosmetics, in particular as a lipstick.

43 Claims, No Drawings

COSMETIC COMPOSITION IN THE FORM OF A SOFT PASTE, A PROCESS FOR ITS PREPARATION AND ITS USE

The present invention is directed to a cosmetic composition in the form of a soft paste, which can be used to care for and/or make up the lips of the face or the skin. The invention is also directed to a process for the preparation of this composition and to its use.

Cosmetic compositions which can be applied to the skin or the lips of the face as a make-up or care product, such as bases for lip products or lipsticks, for example, generally contain fats including waxes and oils, pigments and/or fillers and, optionally, additives.

It is known that the larger the amount of waxes present in the composition, the firmer the consistency of the composition will be, thereby allowing it to be used in stick form. However, the presentation, in particular of a lipstick, in stick form has certain drawbacks: a stick is difficult to use to draw around the contours of the lips and the resistance of the stick to heat is not optimal.

Cosmetic compositions are also known that are in the form of a soft paste, which can be applied, for example, using a brush. These compositions generally contain a small amount of waxes, on the order of 3–8%, and fats, in particular of pasty and oily type. The fats of pasty type are generally present in large amounts, so as to obtain a composition whose consistency and viscosity are suitable and allow the composition to be easily applied. It has been observed, however, that these compositions do not make it possible to apply to the skin a film with good sensory qualities. The reason for this is that certain pasty fats have the drawback of giving the applied film a sticky feel. Furthermore, another drawback of these compositions lies in their capacity to migrate, that is to say, in the fact that they have a tendency to spread within the fine lines of the skin, in particular those around the lips, creating an aesthetically unpleasant effect, this migration being partly due to the presence of oily fats in a large amount.

The present invention aims to overcome the drawbacks of the prior art and to provide a composition which migrates little when it is applied to a support, while at the same time giving a film with very good staying power and which is pleasant to wear.

One subject of the present invention is thus a cosmetic composition in the form of a soft paste, comprising at least one wax and at least one oil thickened by the presence of at least one thickener and at least 6% by weight of fillers.

Another subject of the invention is the use of this composition to obtain a shiny film and/or a film which is of very good staying power and/or which does not transfer and/or which does not stain and/or which does not migrate over time.

Yet another subject of the invention is a process for the preparation of the above composition, which comprises preparing a premix of at least one of the oils with at least one of the thickeners, homogenizing the premix and then adding the rest of the constituents to the homogenized premix.

The composition according to the invention makes it possible to obtain a homogeneous film, which is easy to apply and which spreads easily and uniformly. The film obtained also has a light texture and remains comfortable to wear throughout the day. Another advantage of the composition according to the invention is that, unexpectedly, it allows a film of shiny appearance to be obtained, although this film contains a large amount of fillers, in particular spherical fillers, which are usually known to give the film a matte appearance. Lastly, the film obtained in accordance with the invention has very good staying power, does not transfer and does not stain a support with which it may come into contact, and does not migrate over time.

One of the characteristics of the composition according to the invention is that it contains very few, and preferably does not contain any, oils in liquid form. The reason for this is that it has been observed that the addition of oils in a form which is thickened, or even gelled, by virtue of the presence of a thickener and a large amount of fillers, in particular spherical fillers, makes it at least partly possible to avoid the problem of migration of the film, while at the same time retaining easy application of the composition to the skin, and the suitable sensory qualities. Without being limited by this explanation, it is considered that this effect is due in particular to the charges, which, when they are mixed with the oils, at least partly absorb the oils and lead to their at least partial gelation. This gelled nature is also increased by the presence of at least one thickener in the composition.

The composition according to the present invention is thus a soft paste whose viscosity can be measured, in contrast to the solid structure of a stick whose viscosity cannot be measured. The dynamic viscosity of the compositions of the invention at 25° C. preferably ranges from 3 to 30 Pa s, measured with a Contraves TV rotary viscometer fitted with an "MS-r4" rotor operating at a frequency of 60 Hz.

The composition according to the invention thus comprises at least one wax and at least one oil, which form all or some of the fatty phase. The end melting point of the fatty phase is preferably below 110° C., which does not prevent certain constituents of the fatty phase from being able to have a higher melting point.

Any wax known in the prior art may be used and, preferably, mineral waxes such as microcrystalline waxes, paraffin, petrolatum, petroleum jelly, ozokerite and montan wax; animal waxes such as beeswax, lanolin and derivatives thereof; plant waxes such as candelilla wax, ouricurry wax, carnauba wax, Japan wax, cocoa butter, cork fibre wax or sugar cane wax; hydrogenated oils, fatty esters and glycerides which are solid at 250° C.; synthetic waxes such as polyethylene waxes and the waxes obtained by Fischer-Tropsch synthesis; and silicone waxes. The fatty phase may comprise one wax or a mixture of waxes.

The compositions of the invention preferably comprise from 0.5 to 8% by weight of wax, and more preferably from 1.5 to 6% by weight of wax.

The fatty phase also comprises at least one oil, or a mixture of oils, which are usually used in cosmetics, among which mention may preferably be made of mineral oils such as paraffin oil and liquid petroleum jelly; animal oils such as perhydrosqualene and arara oil; plant oils such as sweet almond oil, beauty-leaf oil, palm oil, castor oil, avocado oil, jojoba oil, olive oil and cereal germ oil; silicone oils; esters of lanolic acid, of oleic acid, of lauric acid, of stearic acid and of myristic acid, for example; alcohols such as oleyl alcohol, linoleyl alcohol, linolenyl alcohol, isostearyl alcohol and octyidodecanol; acetylglycerides, octanoates, decanoates and ricinoleates of alcohols and of polyalcohols.

The composition may comprise up to 93.3% by weight of oil, and preferably comprises from 15 to 80% by weight of oil.

The composition may also comprise other fats such as pasty hydrocarbon compounds, in a low amount.

The fatty phase may represent up to 94% by weight of the composition, and preferably represents from 70 to 90% by weight of the composition.

The composition also comprises at least one thickener, which may preferably be chosen from clays such as bentonites or hectorites, which are optionally modified, in particular with distearyidimethylammonium chloride, stearyldimethylbenzylammonium chloride, aluminium silicates, or magnesium silicates. Hydrogenated castor oil derivatives, such as THIXINR from Rheox, may also be used.

The thickener, and/or the fillers, are present in the compositions of the invention so as to thicken at least some of the oils, preferably all of the oils. It is understood thereby that the mixture "oil+fillers+thickener" has a viscosity preferably ranging from 50 to 250 Pa s, more preferably from 150 to 220 Pa s, measured with a Contraves TV rotor viscometer fitted with an "MS-r5" rotor operating at a frequency of 60 Hz.

The thickener is preferably present in a proportion ranging from 0.2 to 10% by weight, and more preferably in a proportion ranging from 0.5 to 5% by weight, relative to the total weight of the composition.

The composition of the invention also comprises at least 6% by weight, preferably 8 to 25% by weight, of fillers. In the present description, the term fillers is understood to refer to colorless or white, inorganic, organic or synthetic, lamellar or spherical particles intended to give body or rigidity to the composition. In a preferred embodiment of the invention, the fillers are mainly spherical, inorganic and/or organic fillers.

Fillers capable of absorbing at least some of the oils present in the composition are preferably chosen from the usual inorganic or organic fillers, such as talc, mica, silica, kaolin, nylon powder, polyethylene powder, optionally crosslinked starch, boron nitride, hollow microspheres such as Expancel (Nobel Industry), and silicone resin ballotini (Tospearls from Toshiba, for example), and mixtures thereof.

The composition may also comprise pigments and/or pearlescent agents usually used in cosmetics and which are preferably present in a proportion ranging from 0 to 20% by weight, and more preferably in a proportion ranging from 2 to 12% by weight, relative to the total weight of the composition. The term pigments should be understood to refer to white or colored, inorganic or organic particles intended to color and/or opacify the composition. The term pearlescent agents should be understood to refer to iridescent, calcium-rich particles produced in the shell of certain molluscs.

Among these pigments and/or pearlescent agents which may preferably be mentioned are titanium dioxide, zirconium dioxide or cerium dioxide, as well as zinc oxide, iron oxide, chromium oxide and ferric blue; carbon black, and barium, strontium, calcium and aluminium lakes; mica coated with titanium oxide or bismuth oxychloride, as well as titanium mica and natural mother-of-pearl.

The composition may also comprise any additive usually used in the cosmetics field, such as antioxidants, fragrances, essential oils, preserving agents, cosmetic active agents, moisturizers, vitamins, essential fatty acids, sphingolipids, sunscreens, surfactants, liposoluble polymers such as polyalkylenes, polyacrylates and silicone-containing polymers which are compatible with fats. Obviously, a person skilled in the art will take care to select this/these optional additional compounds, and/or the amount thereof, such that the advantageous properties of the compositions according to the invention are not, or are substantially not, altered by the addition envisaged.

The compositions according to the invention find application in particular in the field of applying make-up to the skin, semi-mucous membranes and/or mucous membranes and can be, for example, in the form of a foundation, a blusher, an eye-shadow, a lipstick, a mascara or an eye-liner. They may also be used as a care base for the lips or as a fixing base to be applied to a standard lipstick. The fixing base then forms a protective film on the film of lipstick, limits its transfer and migration and thereby allows its staying power to be increased.

The compositions according to the invention may also be in the form of a care product for the skin, mucous membranes and/or semi-mucous membranes, a pharmaceutical or hygiene product or alternatively an anti-sun or self-tanning product.

One process for the preparation of the compositions according to the invention preferably comprises preparing a premix of at least some of the oils, i.e., at least one oil, with at least some of the thickener, i.e. at least one thickener, homogenizing the premix and then adding the rest of the constituents to the premix. Indeed, it has been observed that, when this process is carried out, the liquid oils, are in some way "trapped", during the homogenization, in a thickened, or even gelled structure, leading to a resulting composition which is more pleasant to apply and wear, and which is of improved staying power, in particular on the lips.

Preferably, all of the oil in the compositions is thickened. The amount, however, of non-thickened oil that may be present in the compositions is preferably less than 5%. More preferably, the amount of non-thickened oil present in the compositions is less than 2%. Most preferably, there is not any non-thickened oil present in the compositions of the invention, i.e., all the oil is thickened. It is also preferable, before homogenization, that the premix comprises all of the oils and/or all of the thickener.

The homogenization may be carried out by any means known to those skilled in the art, in particular by turbo-mixing, that is to say mixing using a turbo-mixer; the homogenization being carried out so as to obtain a thickened premix. Alternatively, after homogenization of the premix, the rest of the constituents, including the fillers, are added and the resulting composition is then mixed, optionally heated, and packaged.

The invention is illustrated in greater detail in, but not limited by, the examples which follow.

EXAMPLE 1

A lip composition in soft paste form having the following composition was prepared:

| | |
|---|---|
| waxes (carnauba wax and beeswax) | 4 g |
| oils (castor oil and octyldodecanol) | 16 g |
| acetylated lanolin | 20 g |
| lanolin | 30 g |
| thickener (Bentone) | 1 g |
| fillers (starch crosslinked with octenyl-succinic anhydride, mica) | 20 g |
| pigments | 9 g |

The composition was prepared in the following way: the oils and the thickener were mixed together in a first stage, the mixture was homogenized using a turbo-mixer so as to obtain a gel, the rest of the constituents were then added and the mixture was heated to about 100° C. while mixing, so as to obtain a perfectly homogeneous mixture.

After cooling, an anhydrous lip composition was obtained, which was easy to apply and which made it possible to obtain a shiny film which was pleasant to wear, was free of any sticky feel and was of good staying power.

EXAMPLE 2

A lip composition in soft paste form having the following composition was prepared:

| | |
|---|---|
| waxes (carnauba wax and ozokerite) | 8 g |
| oils (castor oil and mineral oils) | 29 g |
| lanolin | 40 g |
| thickener (Bentone) | 4 g |
| fillers (silica and talc) | 12 g |
| pigments | 7 g |

The composition was prepared according to Example 1. An anhydrous lip composition was obtained, which was easy to apply and which made it possible to obtain a shiny film which was pleasant to wear and free of any sticky feel.

EXAMPLE 3

A lip composition in soft paste form having the following composition was prepared:

| | |
|---|---|
| waxes (microcrystalline wax and candelilla wax) | 6 g |
| oils (sesame oil and octyl palmitate) | 48 g |
| acetylated lanolin | 25.2 g |
| thickener (THIXINR from Rheox) | 0.8 g |
| fillers (silica, starch and nylon powder) | 15 g |
| pigments | 5 g |

The composition was prepared according to Example 1. A lip composition having good cosmetic properties was obtained.

EXAMPLE 4: COMPARATIVE EXAMPLE

A lip composition in soft paste form having the following composition was prepared:

| | |
|---|---|
| waxes (carnauba wax and ozokerite) | 6 g |
| oils (castor oil and mineral oils) | 64 g |
| acetylated lanolin | 25 g |
| pigments | 5 g |

The composition was prepared according to Example 1. A very oily lip composition was obtained. The film applied to the lips was of very poor staying power and migrated considerably.

EXAMPLE 5: COMPARATIVE EXAMPLE

A lipstick in soft paste form having the following composition was prepared:

| | |
|---|---|
| waxes (carnauba wax and ozokerite) | 6 g |
| oils (castor oil and mineral oils) | 48 g |
| acetylated lanolin | 41 g |
| pigments | 5 g |

The composition was prepared according to Example 1. A very sticky and very pasty lipstick which was unpleasant to apply was obtained. The film applied to the lips had a tendency to migrate.

What is claimed is:

1. A cosmetic composition in the form of a soft paste, comprising:

(a) at least one wax; and (b) at least one oil, wherein said at least one oil is thickened prior to combination with said at least one wax by at least one thickener and at least 6% by weight, relative to the total weight of the composition, of at least one filler.

2. A composition according to claim 1, which comprises from 8 to 25% by weight of said at least one filler.

3. A composition according to claim 1, wherein said at least one filler is a spherical, an inorganic or an organic filler.

4. A composition according to claim 1, wherein said at least one filler is talc, mica, silica, kaolin, nylon powder, polyethylene powder, starch which may be crosslinked, boron nitride, hollow microspheres, silicone resin ballotini or mixtures thereof.

5. A composition according to claim 1, wherein said at least one thickener is present in a proportion ranging from 0.2 to 10% by weight, relative to the total weight of the composition.

6. A composition according to claim 5, wherein said at least one thickener is present in a proportion ranging from 0.5 to 5% by weight, relative to the total weight of the composition.

7. A composition according to claim 1, wherein said at least one thickener is a clay which may be modified or a hydrogenated castor oil derivative.

8. A composition according to claim 7, wherein said clay which may be modified is a bentonite or a hectorite.

9. A composition according to claim 7, wherein said clay is modified with distearyidimethylammonium chloride, stearyidimethylbenzylammonium chloride, an aluminium silicate or a magnesium silicate.

10. A composition according to claim 1, wherein said at least one wax is present in a proportion ranging from 0.5 to 8% by weight, relative to the total weight of the composition.

11. A composition according to claim 10, wherein said at least one wax is present in a proportion ranging from 1.5 to 6% by weight, relative to the total weight of the composition.

12. A composition according to claim 1, wherein said at least one wax is a mineral wax, an animal wax, a plant wax, a hydrogenated oil, a fatty ester, a glyceride which is solid at 25° C., a synthetic wax, a silicone wax, or a mixture thereof.

13. A composition according to claim 12, wherein said mineral wax is a microcrystalline wax, paraffin, petrolatum, petroleum jelly, ozokerite or montan wax.

14. A composition according to claim 1, wherein said animal wax is beeswax, lanolin or a derivative thereof.

15. A composition according to claim 12, wherein said plant wax is candelilla wax, ouricurry wax, carnauba wax, Japan wax, cocoa butter, cork fibre wax, or sugar cane wax.

16. A composition according to claim 12, wherein said synthetic wax is a polyethylene wax or a wax obtained by Fischer-Tropsch synthesis.

17. A composition according to claim 1, wherein said at least one oil is present in an amount which ranges up to 93.3% by weight, relative to the total weight of the composition.

18. A composition according to claim 17, wherein said at least one oil is present in an amount which ranges from 15 to 80% by weight, relative to the total weight of the composition.

19. A composition according to claim 12, wherein said at least one oil is a mineral oil; an animal oil; a plant oil; a silicone oil; an ester of lanolic acid, of oleic acid, of lauric acid, of stearic acid or of myristic acid; an alcohol; an acetylglyceride, an octanoate, a decanoate or a ricinoleate of an alcohol or of a polyalcohol; or a mixture thereof.

20. A composition according to claim 19, wherein said mineral oil is paraffin oil or liquid petroleum jelly.

21. A composition according to claim 19, wherein said animal oil is perhydrosqualene or arara oil.

22. A composition according to claim 19, wherein said plant oil is sweet almond oil, beauty-leaf oil, palm oil, castor oil, avocado oil, jojoba oil, olive oil or cereal germ oil.

23. A composition according to claim 19, wherein said alcohol is oleyl alcohol, linoleyl alcohol, linolenyl alcohol, isostearyl alcohol or octyldodecanol.

24. A composition according to claim 1, which has a dynamic viscosity at 25° C. which ranges from 3 to 30 Pa s.

25. A composition according to claim 1, wherein said at least one oil which has been thickened by said at least one thickener and said at least one filler is greater than or equal to 95% of the total amount of oil present in said composition.

26. A composition according to claim 25, wherein said at least one oil which has been thickened by said at least one thickener and said at least one filler is greater than or equal to 98% of the total amount of oil present in said composition.

27. A composition according to claim 26, wherein all of the oil present in said composition has been thickened by the presence of said at least one thickener and said at least one filler.

28. A composition according to claim 1, wherein said at least one oil and said at least one wax form all or some of a fatty phase, wherein the end melting point of said fatty phase is below 110° C.

29. A composition according to claim 1, which is in the form of a care product or a make-up product for the skin, semi-mucous membranes or mucous membranes.

30. A composition according to claim 29, which is in the form of a care product or a make-up product for the lips.

31. A composition according to claim 1, which is in the form of a foundation, a blusher, an eye-shadow, a lipstick, a mascara, an eye-liner, a care base for the lips, a fixing base to be applied to a lipstick, a care product, a pharmaceutical product, a hygiene product, an anti-sun product or a self-tanning product.

32. A process for the preparation of a composition according to claim 1, which comprises the steps of:
preparing a premix comprising at least one oil, at least one thickener, and at least one filler;
homogenizing said premix; and
adding to said homogenized premix at least one wax, wherein said at least one filler constitutes at least 6% by weight, relative to the total weight of the composition.

33. A process according to claim 32, wherein after said homogenizing step, no additional oil or thickener is added to said premix.

34. A method for applying make-up to the skin or caring for the skin, which comprises applying a cosmetic composition according to claim 1 to the skin.

35. A method of treating lips comprising the step of applying the cosmetic composition according to claim 1, to said lips.

36. A method for preparing a cosmetic film which is shiny and/or has very good staying power and/or does not transfer and/or does not stain and/or does not migrate over time, which method comprises the step of applying to skin or lips a cosmetic composition according to claim 1 to form said cosmetic film.

37. A premix for a cosmetic composition, which comprises at least one oil, wherein said at least one oil is thickened by at least one thickener and wherein said premix has a viscosity ranging from 50 to 250 Pa s.

38. A premix according to claim 37, wherein said viscosity ranges from 150 to 220 Pa s.

39. A premix for a cosmetic composition, which comprises at least one oil, wherein said at least one oil is thickened by at least one filler and wherein said premix has a viscosity ranging from 50 to 250 Pa s.

40. A premix according to claim 39, wherein said viscosity ranges from 150 to 220 Pa s.

41. A premix for a cosmetic composition, which comprises at least one oil, wherein said at least one oil is thickened by at least one oil and at least one filler and wherein said premix has a viscosity ranging from 50 to 250 Pa s.

42. A premix according to claim 41, wherein said viscosity ranges from 150 to 220 Pa s.

43. A cosmetic composition in the form of a soft paste, said composition being prepared by a process comprising the steps of:
preparing a premix comprising at least one oil, at least one thickener, and at least one filler;
homogenizing said premix; and
adding to said homogenized premix at least one wax, wherein said at least one filler constitutes at least 6% by weight, relative to the total weight of the composition.

* * * * *

UNITED STATES PATENT AND TRADEMARK OFFICE
CERTIFICATE OF CORRECTION

PATENT NO. : 5,882,657
DATED : March 16, 1999
INVENTOR(S) : Dolorès MIGUEL-COLUMBEL et al.

It is certified that error appears in the above-identified patent and that said Letters Patent is hereby corrected as shown below:

IN THE CLAIMS:

Column 6, line 29, change "diastearyidimethylammonium" to

--distearyldimethylammonium--

Column 6, lines 29-30, "stearyidimethylammonium" to

--stearyldimethylbenzylammonium--

Signed and Sealed this

Seventh Day of September, 1999

Attest:

Q. TODD DICKINSON

Attesting Officer

Acting Commissioner of Patents and Trademarks